United States Patent [19]

Levin et al.

[11] Patent Number: 4,787,891
[45] Date of Patent: Nov. 29, 1988

[54] SYRINGE HOLDER AND APPLICATOR

[75] Inventors: Paul D. Levin, 1595 Soquel Dr., Santa Cruz, Calif. 95065; John D. Harding, Santa Cruz, Calif.

[73] Assignee: Paul Levin, Santa Cruz, Calif.

[21] Appl. No.: 72,773

[22] Filed: Jul. 13, 1987

[51] Int. Cl.⁴ ............................................. A61M 5/20
[52] U.S. Cl. ..................................... 604/136; 604/187
[58] Field of Search ............... 604/187, 136, 134, 232, 604/218, 207, 223; 128/1.1

[56] References Cited

U.S. PATENT DOCUMENTS

| 3,880,163 | 4/1975 | Ritterskamp | 604/136 |
| 3,941,130 | 3/1976 | Tibbs | 604/136 |
| 4,639,249 | 1/1987 | Larson | 604/198 |

FOREIGN PATENT DOCUMENTS

| 2724391 | 12/1977 | Fed. Rep. of Germany | 604/136 |
| 1080887 | 12/1954 | France | 604/136 |

Primary Examiner—John D. Yasko

[57] ABSTRACT

A syringe holder and applicator provides a unique latch mechanism for mounting a syringe on a slider and loading the syringe into a holder. The latch mechanism pivots on the slider in such a way that it may be engaged and retracted against the force of a spring, pulling the slider into a cocked position, pivoted to a position that allows the syringe to be placed on the slider and mounted in the holder, and then pivoted into the cocked position, locking the syringe to the holder and conditioning the device for administering an injection. The slider and syringe are maintained in a position of retraction against the spring by a detent which may be released by a finger operated contact or trigger button.

12 Claims, 4 Drawing Sheets

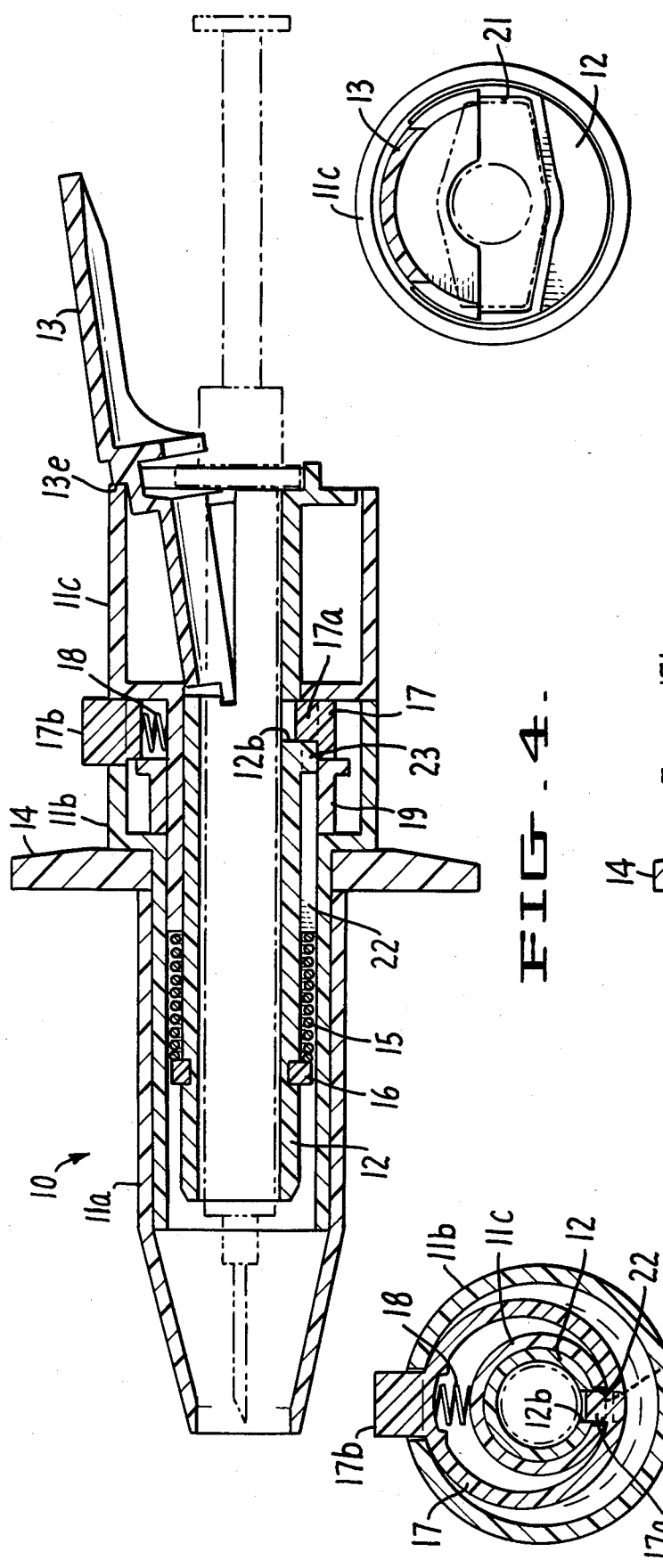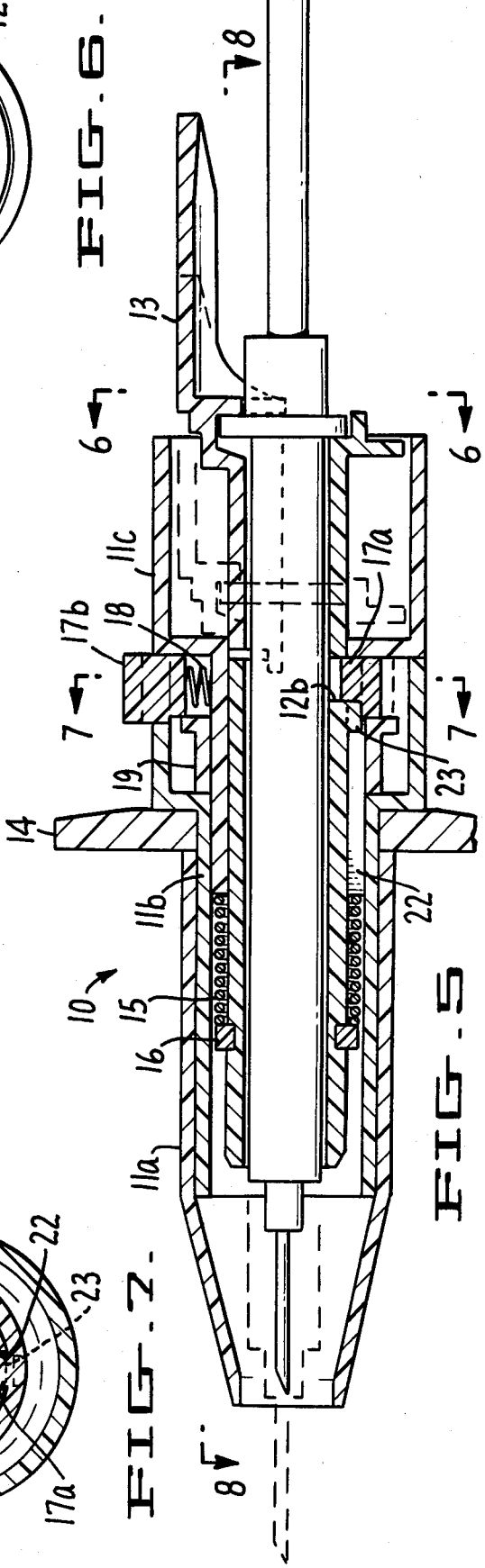

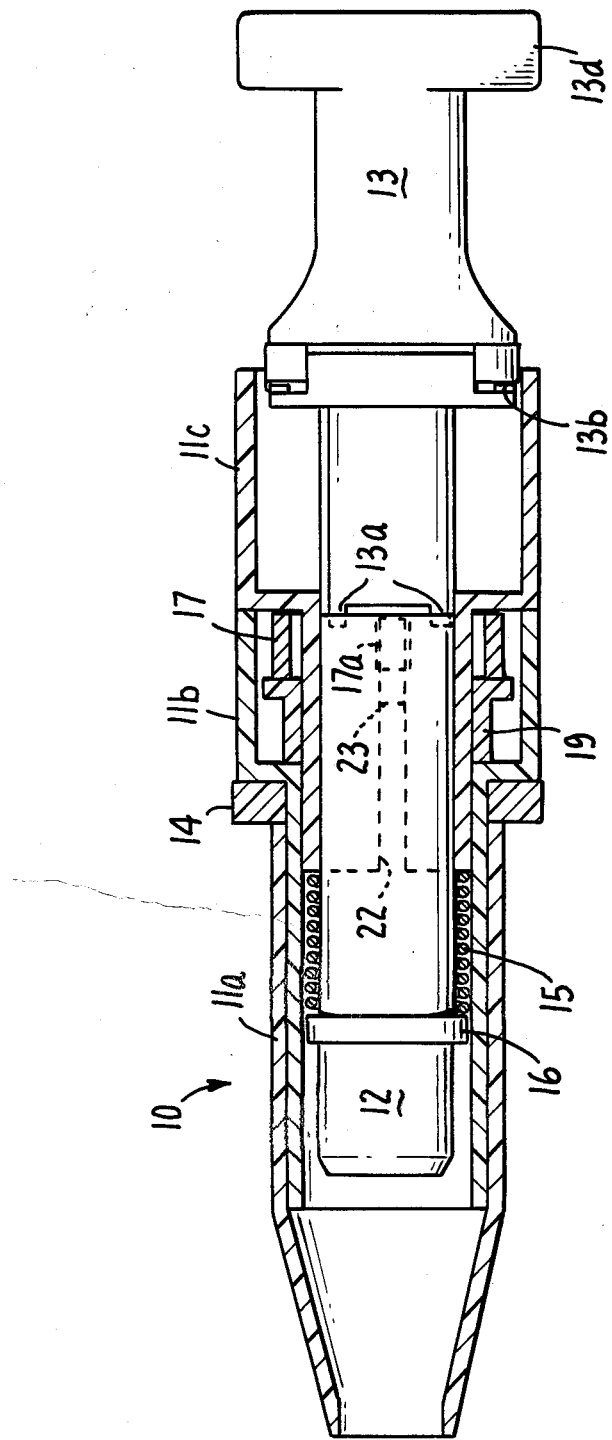
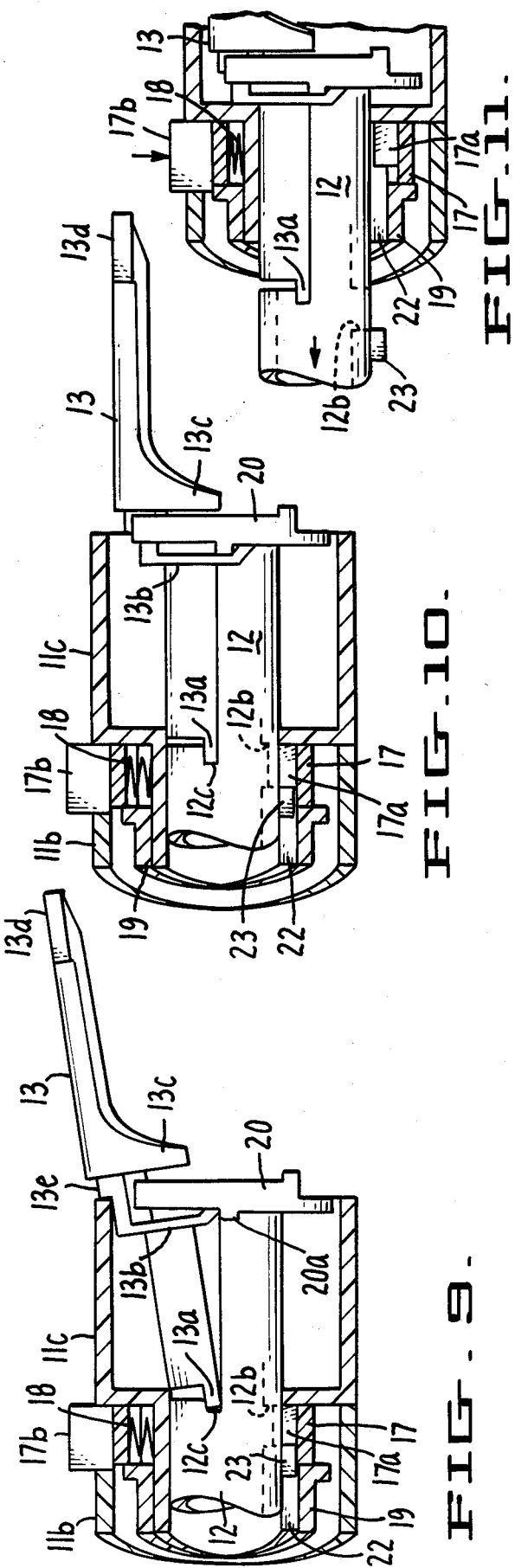

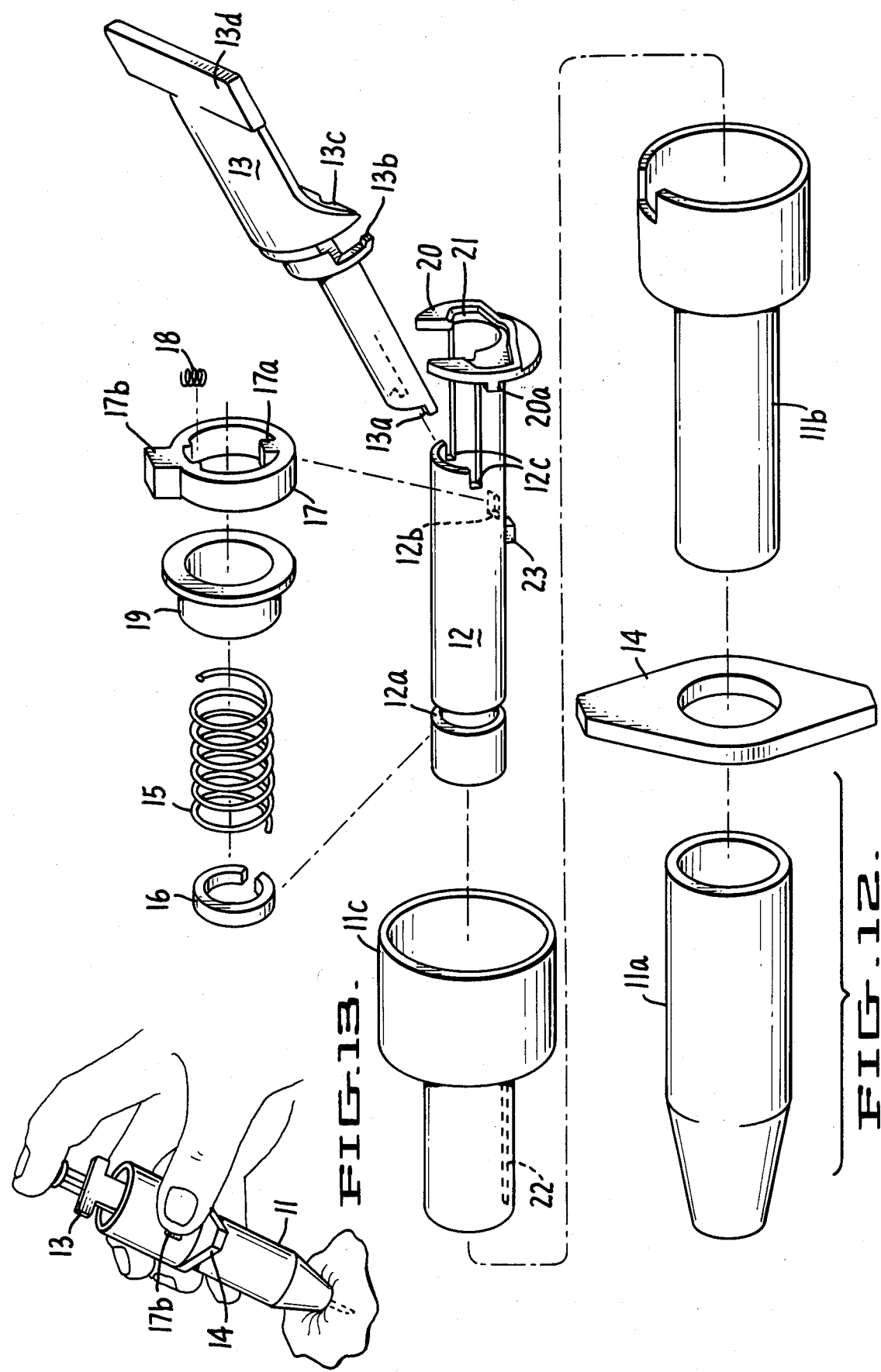

SYRINGE HOLDER AND APPLICATOR

BACKGROUND OF THE INVENTION

Many devices are known and have been developed to assist patients in self-administration of insulin and other medications with hypodermic syringes. The need for such devices arises largely from the psychological difficulty experienced by many patients in striking themselves with a needle. The ideal instrument must be easy to load with a syringe, cause minimal noise in its operation so as not to frighten patients, reduce the discomfort of injection, and any moving part should be so situated or housed as not to interfere with the application and use of the device. In addition, the device should be capable of accepting the syringes of different manufacturers and useful with syringes of different capacities, such as the conventional ½ c.c. and 1 c.c. sizes. It is also desirable that the device be capable of adjusting the depth of injection, particularly for children or for persons having thin skin or subcutaneous tissue. The invention herein described is believed to meet all of these criteria and to be an advance in the state of the art.

BRIEF SUMMARY OF THE INVENTION

A syringe holder and applicator of the present invention provides a unique latch mechanism for mounting a syringe on a slider and loading the syringe into a holder. The latching mechanism is pivoted to the slider in such a way that it may be engaged by the fingers and retracted against the force of a main spring, pulling the slider into a cocked position; the latch is then pivoted into a second position that allows the syringe to be placed on the slider and mounted in the holder; and, finally, the latch is pivoted into its first position, locking the syringe to the holder and conditioning the device for administering an injection. At this time, the slider and syringe are maintained in a position of retraction against the main spring by a detent which may be released by a finger operated contact or trigger button.

The latch mechanism of the present invention, it will be found, is easily accessible for retracting the slider but is out of the way of a patient's hand during the injection process. Thus, the patient's finger cannot rub against moving parts or interfere with an injection. It is believed that the latching mechanism can be used more easily and more rapidly by a patient than other conventional syringe mechanisms.

Various objects of the invention, in addition to those described above, will become apparent in view of the following detailed description.

BRIEF DESCRIPTION OF THE DRAWINGS

In the drawings forming a part of this application and in which like parts are identified by like reference numerals.

FIGS. 4 and 5 are longitudinal sections of the device illustrating two different positions of the pivoted latch lever, FIG. 4 being taken on line 4—4 of FIG. 1 and FIG. 5 being taken on line 5—5 of FIG. 2;

FIG. 6 is a transverse section taken on the line 6—6 of FIG. 5;

FIG. 7 is a transverse section taken on line 7—7 of FIG. 5;

FIG. 8 is a longitudinal section taken on the line 8—8 of FIG. 5;

FIGS. 9 and 10 are partial sections of the device illustrating two different positions of the latch lever for loading and locking a syringe;

FIG. 11 is a partial section illustrating a relationship of parts after the slider and syringe have been advanced;

FIG. 12 is an exploded perspective view of parts; and

FIG. 13 illustrates one manner for holding the device while making an injection.

BRIEF DESCRIPTION OF THE PREFERRED EMBODIMENT

Figure 1:
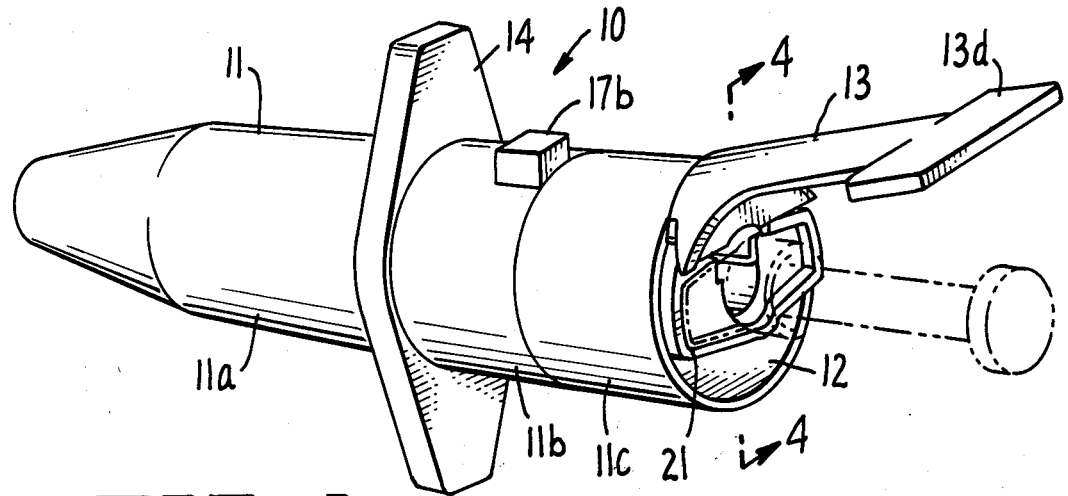
FIGS. 1, 2 and 3 illustrate a preferred embodiment of the device in three different positions of operation.

The drawings illustrate a preferred embodiment of a syringe holder and applicator 10 generally comprising a tubular housing 11, a retractable slider 12 and a latch lever 13. Referring to FIGS. 4–12, housing 11 essentially comprises a three-piece assembly consisting of a tubular nosepiece 11a, a slider housing piece 11b and a latch housing piece 11c. In the preferred embodiment, nosepiece 11a is frictionally engaged with piece 11b allowing the nosepiece to be removed and substituted with a nosepiece of greater or shorter length. This provides a means for adjusting either the depth of penetration of the syringe needle or an adjustment to accommodate syringes of different length or capacity. A flange collar 14 is secured to piece 11b and provides a finger rest for supporting and engaging the applicator while operating the syringe.

In operation, slider 12 and latch lever 13 move axially of the housing under the resilient force of a helical mainspring 15. One end of the spring contacts one end of piece 11c, the other end being in contact with a clip 16 secured in a groove 12a formed in slider 12. Clip 16 also serves as a sliding bearing within the smaller end of piece 11b, thus helping to center slider 12 as it is being reciprocated.

Means is provided for retaining slider 12 and latch 13 in an axial position of retraction against the force of spring 15. More particularly, a control ring 17 is integrally formed with a detent 17a and a finger engageable contact or button 17b. The detent is located on the inside of the ring and the button on the outside, and on the diametrically opposite side of the ring from detent 17b. Ring 17 is received over both slider 12 and the smaller tubular end of housing piece 11c.

Referring to FIG. 12 in particular, slider 12 is formed with an opening 12b that is adapted to receive detent 17a when the slider is retracted into what may be described as a cocked position. Ring 17 is resiliently moved transversely to the axis of the housing by a helical compression spring 18 lodged in a cavity beneath finger contact 17b and seated upon the outer surface of the smaller tubular extension of housing member 11c. Ring 17 is positioned axially within the larger tubular extension of housing member 11b by a flanged collar 19, which allows the ring to move transversely to an extent necessary for engaging and disengaging detent 17a with opening 12b.

Slider 12 and latch lever 13 are uniquely formed to interconnect in a manner that allows the latch lever to pivot on an axis transverse to the housing axis. In that regard, slider 12 is formed with a pair of slots 12c that receive a pair of spaced posts 13a formed at one end of latch lever 13. Slider 12 further provides a slotted seat 20 which is engageable with the flange collar of a syringe. A barrier wall 21 formed on seat 20 generally defines the contour of the finger engageable flange of a conventional syringe. Barrier wall 21 functionally serves to inhibit rotation of the syringe after it is properly placed in the slider.

Latch 13 is also formed with a pair of axially spaced flanges 13b and 13c and a finger bar 13d. Flanges 13b and 13c serve to capture both the seat 20 formed at the end of slider 12 and the finger engageable flange formed on the body of a standard syringe. However, pivotal movement of latch 13 to a position as shown in FIG. 4 allows the standard syringe to either be received through the tubular passage of slider 12 or removed therefrom.

Referring to FIGS. 9 and 10 in particular, it will be seen that flange 13b provides a pair of contacts that engage the undersurface of seat 20; and seat 20 is formed with a pair of ridges 20a over which the contacts pass when latch 13 is moved from the position shown in FIG. 9 to the position shown in FIG. 10, and vice versa. These contacts, together with the posts 13a mounted in slots 12a, provide a resilient tightness of fit between the slider and latch in each of its positions of operation.

Slider housing piece 11c is formed with the longitudinal keyway or slot 22 which receives a key 23 formed on slider 12. Thus, slider 12 is mounted for reciprocal and axial movement relative to the housing but is inhibited or restrained from rotational movement.

Referring to FIG. 4, latch lever 13 is formed with a shoulder 13e that engages the end of housing 11c when pivoted to a position for loading a syringe. Thus, even though the button 17b is actuated as would remove detent 17a from opening 12b, the slider-latch assembly cannot be moved by spring 15.

Figure 2:
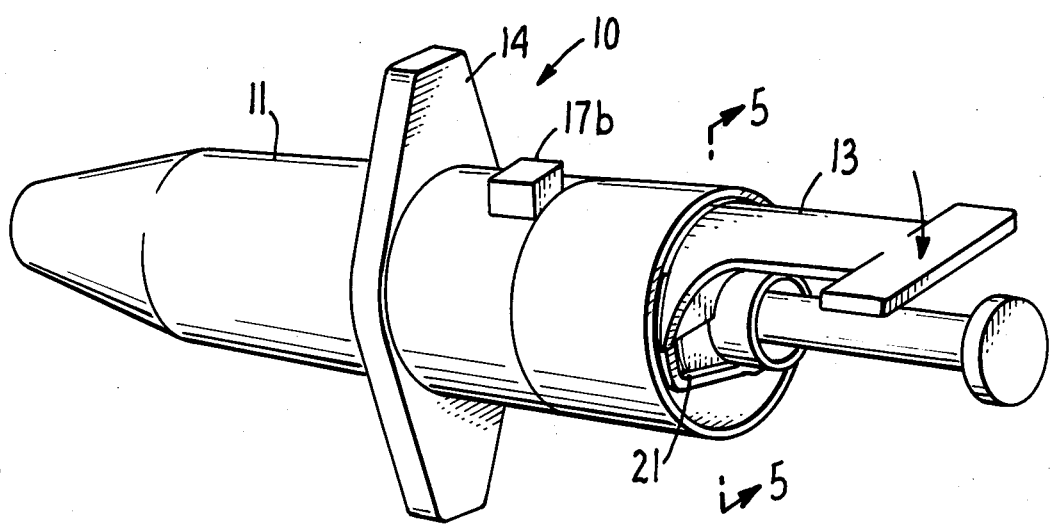
Figure 3:
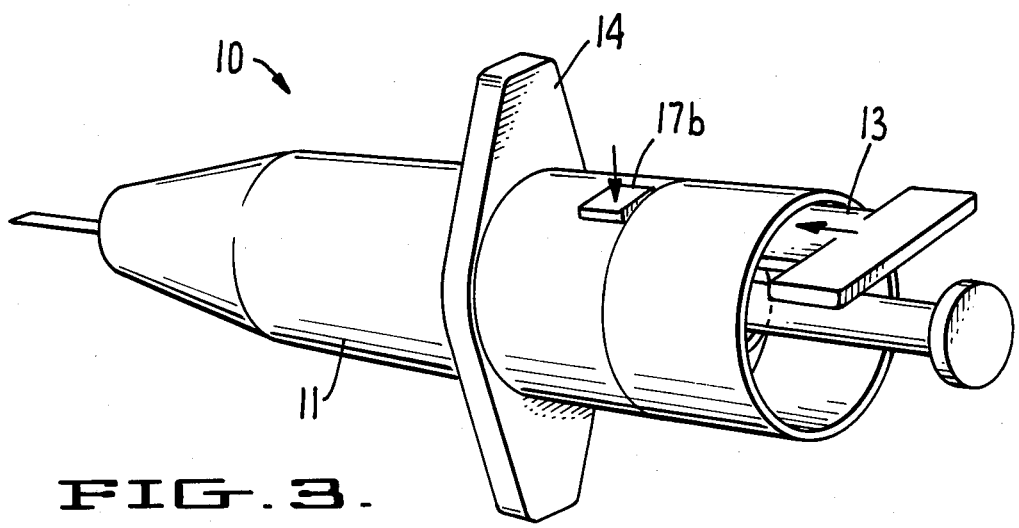

Syringe holder and applicator 10 is operated in the following manner: After a syringe has been filled with the proper dose of insulin or other medication, it is then ready to be placed into applicator 10. First, the latch 13 is pulled upward (as shown in FIG. 2) until the device becomes cocked wherein detent 17 is engaged with opening 12b. Latch lever 13 is then pivoted backward to the position shown in FIGS. 1 and 4, thus rendering the button release inoperative and conditioning the device to receive the syringe. The syringe is then axially inserted into housing 11. Latch 13 is then pivoted into the position shown in FIGS. 2 and 5, thus capturing the flange of the syringe and conditioning the device as a whole for injection.

Referring to FIG. 13, there is shown one method of holding the device wherein the thumb is placed over the trigger. The middle finger is best placed above and the ring finger below the finger rest 14. Holding the end of nosepiece 11a firmly against the skin, button 17b is actuated by the thumb, causing slider 12, latch 13 and the syringe mounted therein to advance under the pressure of spring 15. As shown in FIG. 13, the index finger may then be used to press down on the plunger of the syringe.

Following the injection, latch 13 is pulled upward and pivoted backward to unlock the syringe. The syringe can then be lifted from the device.

Although a preferred embodiment of the invention has been illustrated and described, various modifications and changes may be resorted to without departing from the spirit of the invention or the scope of the appended claims, and each of such modifications and changes is contemplated.

What is claimed is:

1. A syringe holder and applicator comprising:
   a tubular housing;
   slider means for mounting a syringe within said housing for reciprocal movement,
   a finger engageable latch pivotally mounted to said slider means, said latch having a first flange for capturing a syringe in one position and allowing removal of the syringe in a second position,
   spring means for resiliently moving said slider means and latch toward one end of said housing,
   detent means for retaining said slider means and latch in an axial position of retraction against the resilient force of said spring means, and
   a finger engageable contact for moving said detent means to allow said spring means to move said slider means and latch, together with a syringe mounted thereto, within said tubular housing.

2. The syringe holder and applicator of claim 1, and further comprising a flanged finger rest secured to said housing.

3. The syringe holder and applicator of claim 1, said housing comprising a removable nosepiece of selected length, the length being selected to control the depth of penetration of a syringe needle and to operate with a syringe of a particular length.

4. The syringe holder and applicator of claim 1, said latch being engageable with said housing in said second position to prevent axial movement of said slider.

5. The syringe holder of claim 1, said slider means having a slotted seat at one end and engageable with the flanged collar of a syringe, whereby pivotal positioning of said latch in said one position allows the flanged collar of the syringe to be inserted into said slider and placed in contact with said seat.

6. The syringe holder of claim 5, said finger engageable latch being formed with a second flange axially spaced from said first flange and capturing the slotted seat of said slider means, whereby axial movement of said latch or slider means imparts axial movement to the other.

7. The syringe holder of claim 5, said tubular housing comprising a coaxial assembly of a nosepiece, a slider housing piece and a latch housing piece, the end of said latch housing piece being tubular and receivable axially within the slider housing piece, said slider means being keyed to said latch housing piece for relative longitudinal movement with a close sliding fit, and a spring seat mounted to said slider means, said seat being receivable within said slider housing piece with a close sliding fit, whereby said slider housing piece and latch housing piece provide close sliding fits to enhance reciprocation of said slider means.

8. The syringe holder of claim 5, said tubular housing being formed with a longitudinal keyway, said slider means being formed with a key received in said keyway.

9. The syringe holder of claim 1, said finger engageable contact and detent means being integrally formed on a ring mounted around said slider means, said detent means being formed on the inside of said ring and engageable with an opening in said slider means, and a spring urging said ring transversely of said housing for engaging said detent with the opening in said slider means.

10. The syringe holder of claim 1, said slider means being substantially tubular and formed with a pair of pivot slots, said latch being formed with a pair of posts engageable with said pivot slots, whereby said latch may be pivoted while said posts are engaged with said slots.

11. The syringe holder of claim 1, said slider means having a slotted seat at one end and engageable with the flange collar of a syringe, whereby pivotable positioning of said latch in said one position allows the flange collar of the syringe to be inserted into said slider and placed in contact with said seat; said finger engageable latch being formed with a second flange axially spaced from said first flange, whereby pivotal positioning of said latch in the one position captures the slotted seat of said slider means, axial movement of said latch or slider means imparting axial movement to the other.

12. The syringe holder of claim 11, said slotted seat of said slider means and said second flange of said latch having surfaces of engagement that retain said slider means and latch positions of pivotal attachment.

* * * * *